United States Patent [19]
Shilling et al.

[11] Patent Number: 5,456,247
[45] Date of Patent: Oct. 10, 1995

[54] METHOD FOR DELIVERING DRUGS SOLUBLE IN A VAPORIZATION VEHICLE

[75] Inventors: Lynndon J. Shilling, Des Moines; H. M. Stahr, Ogden, both of Iowa

[73] Assignee: Iowa State University Research Foundation, Inc., Ames, Iowa

[21] Appl. No.: 112,671

[22] Filed: Aug. 26, 1993

[51] Int. Cl.$^6$ ................................................ A61M 15/00
[52] U.S. Cl. .................................. 128/203.12; 128/203.27
[58] Field of Search ........................ 128/203.12, 203.26, 128/203.27, 203.15

[56]     References Cited
U.S. PATENT DOCUMENTS

| | | | |
|---|---|---|---|
| 1,323,181 | 11/1919 | Goodfellow | 128/203.27 |
| 1,998,327 | 4/1935 | McGuire | 128/203.27 |
| 4,770,168 | 9/1988 | Rusz et al. | 128/203.27 |
| 4,947,802 | 8/1990 | Fisinin et al. | 119/160 |
| 4,951,659 | 8/1990 | Weiler et al. | 128/200.18 |
| 5,186,164 | 2/1993 | Raghuprasad | 128/203.15 |

Primary Examiner—Edgar S. Burr
Assistant Examiner—Aaron J. Lewis
Attorney, Agent, or Firm—Tilton, Fallon, Lungmus & Chestnut

[57]        ABSTRACT

This invention relates to a method for delivering drugs sublimable in a vaporization vehicle. The method involves combining a sufficient amount of a vaporization vehicle to sublime the drug and the drug to be delivered, heating the vaporization vehicle to substantially its boiling point and administering the vapor by inhalation to a subject.

8 Claims, 1 Drawing Sheet

METHOD FOR DELIVERING DRUGS SOLUBLE IN A VAPORIZATION VEHICLE

BACKGROUND OF THE INVENTION

1. Field of the Invention

This invention relates to a method for delivering drugs soluble in a vaporization vehicle. More particularly, this invention relates to a method for delivering soluble volatilizing drugs to subjects. The present method can be characterized by rapid site respiratory specific delivery of the drug.

2. Description of the Prior Art

In general the prior art relates to means for delivering drugs in the form of very small liquid drops. These means include ultrasonic nebulization, vortex jet nebulization, and vacuum entrainment. In these instances the drugs are delivered as an aerosol. See e.g. Fisinin et al., U.S. Pat. No. 4,947,802. Certain prior art documents show a preheater for nebulizing a liquid, but this heating process is not designed to vaporize the drug. See e.g. Weiler et al., U.S. Pat. No. 4,951,695.

Additional prior methods to deliver drugs involve simply adding the drugs to water or feed. Both types of prior drug delivery methods suffer from the same drawback in that high levels of drug residues become incorporated into the animal's tissue and then will be subsequently consumed in the animal meat. As such a need exists in the industry to develop a drug delivery system that is effective without these harmful side effects.

SUMMARY OF THE INVENTION

This invention provides a process for delivering drugs to a subject characterized by the steps of: a) combining a sufficient amount of a vaporization vehicle to solubilize the drug and a drug to be delivered; b) heating the vaporization vehicle to substantially its boiling point; and administering the vapor by inhalation to the subject. The drugs to be used in this process include sulfamethazine, sulfamethoxazole, sulfadimethoxine and gentamicin. These drugs volatilize at a temperature between about 180° to 200° C. and are administered for up to 5 minutes to obtain 0.2 ppm in a subject's blood. In the preferred embodiment, the vaporization vehicle is a terpene such as menthol, carvone, methone, or camphor.

The invention also provides a process for delivering drugs soluble to a subject characterized by the steps of: a) combining a sufficient amount of terpene to solubilize a drug and a drug to be administered; b) heating the terpene to substantially its boiling point; and administering the vapor by inhalation to the subject. The drugs to be used in this process include sulfamethazine, sulfamethoxazole, sulfadimethoxine and gentamicin. These drugs volatilize between 180° to 200° C. and are administered for up to 5 minutes to obtain 0.2 ppm in a subject's blood. In the preferred embodiment, the vaporization vehicle is a terpene such as menthol, carvone, methone or camphor.

DETAILED DESCRIPTION OF THE INVENTION

Figure 1:
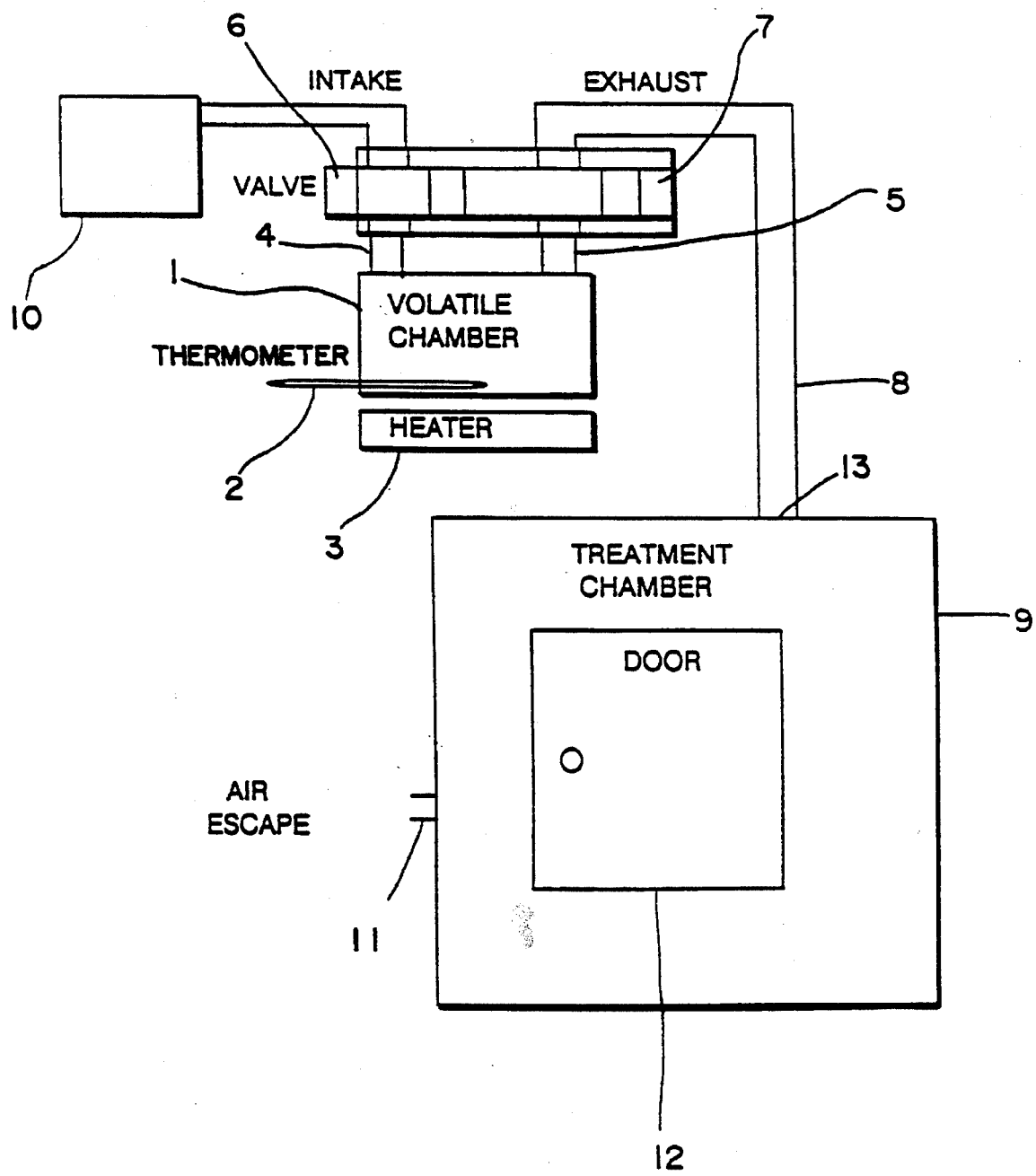
FIG. 1 shows a schematic drawing of a drug delivery apparatus.

This method provides a means of administering the drug deep into the lungs and into the blood stream almost instantaneously. This method does not create the high levels of sulfa residues in meat like the previously discussed prior art methods.

Now referring to FIG. 1, a schematic drawing of a drug delivery apparatus is shown. To begin, a volatile chamber 1 which can allow for visual observation of the drug and vehicle is used. A thermometer 2 is placed on the inside surface of the volatile chamber 1 where the outside surface is being heated by heater 3. At the top of the volatile chamber, there is one inlet 4 and one exhaust opening 5. These openings have valves 6 and 7 on them. The inlet valve 6 is air tight, where the exhaust valve 7 is obstructive but not air tight. Both of these valves 6 and 7 should open at the same time with a single action opening device. The inlet valve 6 allows low pressure air to flow into the volatile chamber 1 and out the exhaust valve 7 carrying the treated air. The air is pressurized by air pump 10. The exhaust tube 8 enters treatment chamber 9 which restricts the air flow that passes from the volatile chamber 1, by inlet hole 13. Animals are placed into treatment chamber 9 through door 12.

The present invention is directed to a method of delivering volatile drugs for treatment of domestic animals or mammals using the above described instrument. More specifically, the invention is directed to a method of volatilizing drugs at temperatures below their boiling point. This objective is achieved by volatilizing the drug in the presence of a vaporization vehicle as the vehicle sublimes. The vaporization vehicle is a compound which sublimes and causes the drug to volatilize below its boiling point. The vaporization vehicle allows the volatilization of the drug at temperatures below its normal melting point.

This concept was originally tested with equal parts of sulfamethazine and menthol in the vapor chamber. Sulfamethazine has a melting point of 176° to 207° C. It should be noted that boiling points of compounds are usually 150°–200° C. higher than most melting points. Using menthol as a vaporization vehicle, however sulfamethazine will volatilized between 180°–200° C., which is a temperature closer to its melting point. This occurred because the vaporization vehicle (menthol) has a melting point of between 41° to 43° C. and a boiling point of 212° C. so as the compounds mix the vaporization vehicle carries the sulfamethazine into the air as it reaches its boiling point.

Drug treatment levels achieved via volatilization have been found by the present inventors to be higher than oral treatment levels. Moreover, when the drug is administered according to the present method the drug is delivered to blood and specific organs, while with conventional water delivery the drug is found throughout the animal. Specifically, drug levels were attained that were twice the amount previously obtained from the oral intake of the drug in water. The oral intake was systemic, but caused higher drug residues in the meat. The critical factor with this inhalation therapy is limited contact time, since the lungs inhale and exhale. Tests revealed that once the treatment is stopped, twenty five minutes later only half the level of sulfa can be detected.

The results of sulfamethazine inhalation therapy in lung tissue show that if taken orally, (dissolved in water) the results were 0.1 ppm (parts per million). But if taken through inhalation the immediate levels were 0.2 ppm and were reduced to 0.1 ppm twenty five minutes later. The levels that were taken orally were administered for a period of time on the order of days, while inhalation treatments were for a period of time on the order of minutes in length (five minutes).

The present method is capable of volatilizing drugs such as sulfamethazine, sulfamethoxazole, sulfadimethoxine, and gentamicin. All of these drugs volatilize between 180°–200°

C. with this method. The amount of vaporization vehicle depends on which drug is delivered. More specifically, if menthol is the vaporization vehicle about 0.5 grams of sulfamethoxazole solubilizes in 0.125 grams of menthol, while 0.5 grams of sulfamethazine solubilize in 0.250 grams of menthol. Certain drugs such as gentamicin can be volatilized with little or no menthol. Generally, the proportions of the drug to the volatilizing vehicle are determined experimentally with equal parts of the volatilizing vehicle such as menthol with about five grams of drugs as the starting point for ascertaining the proportions. Other potential vaporization vehicles include carvone, menthone and camphor.

This method for example may be useful in the treatment of bordetella avium disease in turkeys. The two drugs that have been successful at treating the disease, are capable of being volatilized. These are gentamicin and sulfamethoxazole.

Example 1

Tests were conducted to study the entry of sulfa drugs into the blood and lungs of test subjects. Referring now to FIG. 1 heater 3 was activated to a predetermined setting. Samples of sulfamethazine and menthol (0.285 grams equal portions of each) were weighed and heated to 180° C. in a distillation flask in the volatile chamber 1. Rats were placed in the treatment chamber 9. The lid to the treatment chamber 9 had an inlet hole 13 connected to a tube 8 from exhaust outlet 5 of the volatile chamber 1.

An air pump was used to circulate air through the volatile chamber 10 to the treatment chamber. The rats' condition, temperature of the flask and vapor flow into the treatment chamber 9 were monitored. After three minutes of inhalation therapy the air flow was shut off and the rats were removed from treatment chamber 9.

Blood and lung tissue were removed for testing. The results are shown in Table 1.

TABLE 1

| Delivery of Sulfamethazine | | | |
|---|---|---|---|
| Rat #7 | Lungs:NDA*<br>Blood:NDA | Rat #8 | Lungs:NDA<br>Blood:NDA |
| Rat #9 | Lungs:NDA<br>Blood:1 ppm | Rat #10 | Lungs:Trace<br>Blood:1 ppm |
| Rat #11 | Lungs:Trace<br>Blood:1 ppm | Rat #12 | Lungs:Trace<br>Blood:1 ppm |
| Rat #13 | Lungs:NDA<br>Blood:1 ppm | Rat #14 | Lungs:NDA<br>Blood:0.1 ppm |
| Rat #15 | Lungs:NDA<br>Blood:0.1 ppm | Rat #16 | Lungs:NDA<br>Blood:0.2 ppm |
| Rat #17 | Lungs:Trace<br>¯0.1 ppm<br>Blood:0.2 ppm | Rat #18 | Lungs:Trace<br>¯0.1 ppm<br>Blood:0.2 ppm |

*No detectable amount

Example 2

Tests were conducted to study the entry of sulfa drugs into the blood and lungs of test subjects. Referring now to FIG. 1 heater 3 was activated to a predetermined setting. Samples of sulfamethazine and menthol (0.285 grams equal portions of each) were weighed and heated at 180° C. in a distillation flask in the volatile chamber. Rats were placed in the treatment chamber 9. The lid to the treatment chamber 9 had an inlet hole 13 connected to a tube 8 from exhaust outlet 5 of the volatile chamber 1.

An air pump was used to circulate air through the volatile chamber 10 to the treatment chamber. The rats' condition, temperature of the flask and vapor flow into the treatment chamber 9 were monitored. After three minutes of inhalation therapy the air flow was shut off and the rats were removed from treatment chamber 9. Blood and lung tissue were removed for testing. The results are shown in Table 2.

TABLE 2

| Delivery of Sulfamethazine | | | |
|---|---|---|---|
| Rats # | Tissue | Lungs | Blood |
| 1, 2, 3, 4 | NDA | NDA | NDA |
| 5 | NDA | 30 ppb | NDA |
| 6 | Trace | 50 ppb | NDA |
| 7 | NDA | 50 ppb | 50 ppb |
| 8 | NDA | 100 ppb | 50 ppb |
| 9 | NDA | 50 ppb | 150 ppb |
| 10 | NDA | 25 ppb | 150 ppb |
| 11 | NDA | 50 ppb | 50 ppb |
| 12 | NDA | Trace | 100 ppb |
| 13 | NDA | Trace | NDA |

Example 3

A test was conducted to study the volatility of sulfamethoxazole when suspended as a vapor into the air of the volatile and treatment chamber. Air samples were taken to determine the levels of sulfamethoxazole. Referring now to FIG. 1 heater 3 was activated to the predetermined setting. Samples of sulfamethoxazole and menthol (0.285 grams equal portions of each) were weighed and heated to 180° C. in a distillation flask or volatile chamber. Once the samples started to change chemical state from solid to a liquid air sample #1 was taken directly above the material. Air sample #2 was taken at the same time but higher up in the volatile chamber. The volatile chamber was then subjected to the air flow source. At 30 seconds air sample #3 was taken from the middle of the treatment chamber and again at the 1 minute point air sample #4 was taken from the treatment chamber. At this time the entire treatment chamber was visually filled with the vapor. The results, are shown in Table 3.

TABLE 3

| Delivery of Sulfamethoxazole | |
|---|---|
| Sample # | Results |
| Air 1 | 5 μg |
| Air 2 | NDA |
| Air 3 | NDA |
| Air 4 | 2.5 μg |
| Swab 1 | 10 μg |
| Swab 2 | 10 μg |

Standards 5, 10, & 20 μg

Although the invention has been described primarily in connection with special and preferred embodiments, it will be understood that it is capable of modification without departing from the scope of the invention. The following claims are intended to cover all variations, uses or adaptations of the invention, following, in general, the principles thereof and including such departures from the present disclosure as come within known or customary practice in the field to which the invention pertains, or as are obvious to persons skilled in the field.

We claim:

1. A method for delivering a drug soluble in a vaporization vehicle to a subject, the method comprising the steps of:

a) combining a sufficient amount of a vaporization vehicle selected from the group consisting of: menthol, carvone, menthone and camphor to solubilize a drug selected from the group consisting of: sulfamethazine, sulfamethoxazole, sulfadimethoxine and gentamicin and a drug to be delivered;

b) heating said vaporization vehicle to substantially its boiling point; and c) administering said vapor by inhalation to said subject.

2. The method of claim 1 wherein said drugs volatilize between about 180° to 200° C.

3. The method of claim 1 wherein said drugs are administered for up to 5 minutes to obtain 0.2 ppm in subject blood.

4. The method of claim 1 wherein the vaporization vehicle is a terpene.

5. A method for delivering a drug soluble in a terpene to a subject, the method comprising the steps of:

a) combining a sufficient amount of a terpene to solubilize a drug selected from the group consisting of: sulfamethazine, sulfamethoxazole, sulfadimethoxine and gentamicin and a drug to be delivered;

b) heating said terpene to substantially its boiling point; and c) administering said vapor by inhalation to said subject.

6. The method of claim 5 wherein said drugs volatilize between about 180° to 200° C.

7. The method of claim 5 wherein said drugs are administered for up to 5 minutes to obtain 0.2 ppm in a subject's blood.

8. The method of claim 5 wherein the terpene is selected from the group consisting of: menthol, carvone, menthone, and camphor.

* * * * *